US00PP30897P2

(12) United States Plant Patent
Ibanez

(10) Patent No.: US PP30,897 P2
(45) Date of Patent: Sep. 24, 2019

(54) VERBENA PLANT NAMED 'RIKA1832M3'

(50) Latin Name: *Verbena hybrida*
Varietal Denomination: RIKA1832M3

(71) Applicant: Petra Ibanez, Oceanside, CA (US)

(72) Inventor: Petra Ibanez, Oceanside, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/998,152

(22) Filed: Jul. 10, 2018

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Verbena* plant named 'RIKA1832M3', characterized by its outwardly spreading to mounding plant habit; vigorous growth habit; freely branching habit; dark green-colored leaves; freely flowering habit; relatively large white-colored flowers that are held above and beyond the foliar plane; and relative tolerance to Powdery Mildew (*Podosphaera xanthii*).

1 Drawing Sheet

Botanical designation: *Verbena hybrida.*
Cultivar denomination: 'RIKA1832M3'.

BACKGROUND OF THE INVENTION

The present invention relates to a new and distinct cultivar of *Verbena* plant, botanically known as *Verbena hybrida*, and hereinafter referred to by the name 'RIKA1832M3'.

The new *Verbena* plant is a naturally-occurring branch mutation of *Verbena hybrida* 'RIKA18302M', disclosed in U.S. Plant Pat. No. 29,640. The new *Verbena* plant was discovered and selected by the Inventor on a single flowering plant from within a population of plants of 'RIKA18302M' in a controlled greenhouse environment in Bonsall, Calif. on May 18, 2016.

Asexual reproduction of the new *Verbena* plant by vegetative terminal cuttings in a controlled environment in Bonsall, Calif. since May 24, 2016, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKA1832M3'. These characteristics in combination distinguish 'RIKA1832M3' as a new and distinct *Verbena* plant:

1. Outwardly spreading to mounding plant habit.
2. Vigorous growth habit.
3. Freely branching habit.
4. Dark green-colored leaves.

5. Freely flowering habit.
6. Relatively large white-colored flowers that are held above and beyond the foliar plane.
7. Relatively tolerant to Powdery Mildew (*Podosphaera xanthii*).

Plants of the new *Verbena* can be compared to plants of the mutation parent, 'RIKA18302M'. Plants of the new *Verbena* differ primarily from plants of 'RIKA18302M' in flower color as plants of 'RIKA18302M' have light violet blue and white bi-colored flowers.

Plants of the new *Verbena* can be compared to plants of the *Verbena hybrida* 'AKIV572-1', disclosed in U.S. Plant Pat. number 23,050. In side-by-side comparisons, plants of the new *Verbena* differ primarily from plants of 'AKIV572-1' in the following characteristics:

1. Plants of the new *Verbena* are more vigorous than plants of 'AKIV572-1'.
2. Plants of the new *Verbena* have larger flowers than plants of 'AKIV572-1'.
3. Plants of the new *Verbena* and 'AKIV572-1' differ in flower color as plants of 'AKIV572-1' have light lavender-colored flowers.
4. Plants of the new *Verbena* are more tolerant to Powdery Mildew than plants of 'AKIV572-1'.

Plants of the new *Verbena* can be compared to plants of the *Verbena hybrida* 'Vepita Lavender Ice', not patented. In side-by-side comparisons, plants of the new *Verbena* differ primarily from plants of 'Vepita Lavender Ice' in the following characteristics:

1. Plants of the new *Verbena* are more freely branching than plants of 'Vepita Lavender Ice'.
2. Plants of the new *Verbena* have larger flowers than plants of 'Vepita Lavender Ice'.
3. Plants of the new *Verbena* are more tolerant to Powdery Mildew than plants of 'Vepita Lavender Ice'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant. The photograph at the bottom of the sheet comprises a side perspective view of a typical flowering plant of 'RIKA1832M3' grown in a container. The photograph at the top of the sheet is a close-up view of a typical flowering plant of 'RIKA1832M3'.

DETAILED BOTANICAL DESCRIPTION

The aforementioned photographs and following observations and measurements describe plants grown during the early spring in 10-cm containers in an acrylic-covered greenhouse in Carleton, Mich. and under cultural practices typical of commercial *Verbena* production. During the production of the plants, day and night temperatures ranged from 18° C. to 24° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'RIKA1832M3'.

Parentage: Naturally-occurring branch mutation of *Verbena hybrida* 'RIKA18302M', disclosed in U.S. Plant Pat No. 29,640.

Propagation:

- *Type cutting.*—Vegetative terminal cuttings.
- *Time to initiate roots, summer.*—About three days at temperatures ranging from about 16° C. to 29° C.
- *Time to initiate roots, winter.*—About four days at temperatures ranging from about 16° C. to 21° C.
- *Time to produce a rooted plant, summer.*—About 15 days at temperatures ranging from about 16° C. to 29° C.
- *Time to produce a rooted plant, winter.*—About 20 days at temperatures ranging from about 16° C. to 21° C.
- *Root description.*—Medium in thickness, fibrous; typically white in color, actual color of the roots is dependent on substrate composition, water quality, fertilizer type and formulation, substrate temperature and physiological age of roots.
- *Rooting habit.*—Freely branching; medium density.

Plant description:

- *Plant and growth habit.*—Outwardly spreading to mounding plant habit; freely branching habit with about nine primary lateral branches each with about four to six secondary lateral branches developing per plant; pinching is not required; dense and bushy plant habit; vigorous growth habit.
- *Plant height, soil level to top of foliar plane.*—About 11 cm.
- *Plant height, soil level to top of floral plane.*—About 13.5 cm.
- *Plant diameter* (*spread*).—About 32 cm by 46 cm.

Lateral branch description:

- *Length.*—Variable, about 26 cm.
- *Diameter.*—About 2.5 mm.
- *Internode length.*—About 2.3 cm.
- *Orientation.*—Initially upright then outwardly spreading to turning upright distally.
- *Strength.*—Strong.
- *Texture and luster.*—Pubescent; matte.
- *Color, developing.*—Close to 146C.
- *Color, developed.*—Close to 146B.

Leaf description:

- *Arrangement.*—Opposite, simple.
- *Length.*—About 5.5 cm.
- *Width.*—About 2.8 cm.
- *Shape.*—Deltoid, elongated.
- *Apex.*—Acute.
- *Base.*—Truncate.
- *Margin.*—Crenate.
- *Texture and luster, upper and lower surfaces.*—Hirsute; matte.
- *Venation pattern.*—Pinnate; reticulate.
- *Color.*—Developing leaves, upper surface: Close to N137A. Developing leaves, lower surface: Close to 146C. Fully expanded leaves, upper surface: Close to N137A; venation, close to 147B. Fully expanded leaves, lower surface: Close to 147B; venation, close to 147C.
- *Petioles.*—Length: About 7 mm. Diameter: About 2 mm. Strength: Moderately strong. Texture and luster, upper and lower surfaces: Pubescent, minute; matte. Color, upper and lower surfaces: Close to 147C.

Flower description:

- *Flower arrangement and habit.*—Sessile salverform flowers arranged in upright hemispherical terminal racemes; flowers face upward or outwardly; freely flowering habit with about 30 flowers developing per inflorescence and typically more than 1,000 flowers developing per plant.
- *Natural flowering season.*—Plants flower continuously from spring until frost in Michigan; early flowering habit, plants begin flowering about six weeks after planting.
- *Flower longevity.*—Flowers last about four to five days on the plant; flowers not persistent.
- *Fragrance.*—None detected.
- *Inflorescence height.*—About 3.5 cm.
- *Inflorescence diameter.*—About 6.8 cm.
- *Flower buds.*—Length: About 1.8 cm. Diameter: About 4 mm. Shape: Elongated oblong. Texture and luster: Pubescent, minute; matte. Color: Close to 155D.
- *Flower diameter.*—About 2.4 cm.
- *Flower depth* (*height*).—About 3.2 cm.
- *Throat diameter.*—About 2 mm.
- *Tube length.*—About 3 cm.
- *Tube diameter, distally.*—About 2 mm.
- *Corolla.*—Arrangement: Single whorl of five fused petals fused towards the base into a slender narrow tube. Petal lobe length: About 1.1 cm. Petal lobe width: About 1.1 cm. Petal lobe shape: Roughly cordate. Petal lobe apex: Emarginate. Petal margin: Entire; moderately undulate.
- *Petal texture and luster, upper surface.*—Smooth, glabrous; matte.
- *Petal texture and luster, lower surface.*—Pubescent, minute; matte.
- *Throat texture and luster.*—Pubescent; matte.
- *Tube texture and luster.*—Scattered pubescence, minute; slightly glossy. Color: Petal, when opening, upper surface: Close to NN155A. Petal, when opening, lower surface: Close to NN155D. Petal, fully opened, upper surface: Close to NN155D; towards the throat, tinted with close to 151D; venation, close to NN155D; color does not change with development. Petal, fully opened, lower surface: Close to NN155D; venation, close to NN155D; color does not change with development. Throat: Close to 145C; venation, close to 145C. Tube: Close to 160D; venation, close to 160D.

*Calyx.*—Arrangement: Single whorl of five fused sepals fused towards the base into a slender tube. Length: About 1.6 cm. Diameter: About 3 mm. Sepal length: About 1.4 cm. Sepal width: Less than 1 mm. Sepal shape: Narrowly lanceolate. Sepal apex: Acute. Sepal margin: Entire. Sepal texture and luster, inner surface: Smooth, glabrous; slightly glossy. Sepal texture and luster, outer surface: Pubescence, minute; matte. Sepal color, when opening, upper surface: Close to 147B. Sepal color, when opening, lower surface: Close to 148C. Sepal color, fully opened, upper surface: Close to 147B. Sepal color, fully opened, lower surface: Close to 146B to 146C.

*Peduncles.*—Length: About 3.5 cm. Diameter: About 2 mm. Strength: Strong. Aspect: Upright. Texture and luster: Pubescent; matte. Color: Close to 146C.

*Reproductive organs.*—Stamens: Quantity and arrangement: Four per flower, filaments partially adnate to corolla tube. Filament length: About 1.4 cm. Filament color: Close to 145D. Anther shape: Round. Anther size: About 1 mm by 1 mm. Anther color: Close to 151D. Pollen amount: Scarce. Pollen color: Close to 151D. Pistils: Quantity: One per flower. Pistil length: About 2.5 cm. Stigma shape: Bi-parted. Stigma diameter: About 1 mm. Stigma color: Close to 146A. Style length: About 2 cm. Style color: Close to 145D. Ovary color: Close to 144B. Fruits and seeds: To date, fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8a to 11b.

Pathogen & pest resistance: Plants of the new *Verbena* have been observed to be relatively tolerant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'RIKA1832M3' as illustrated and described.

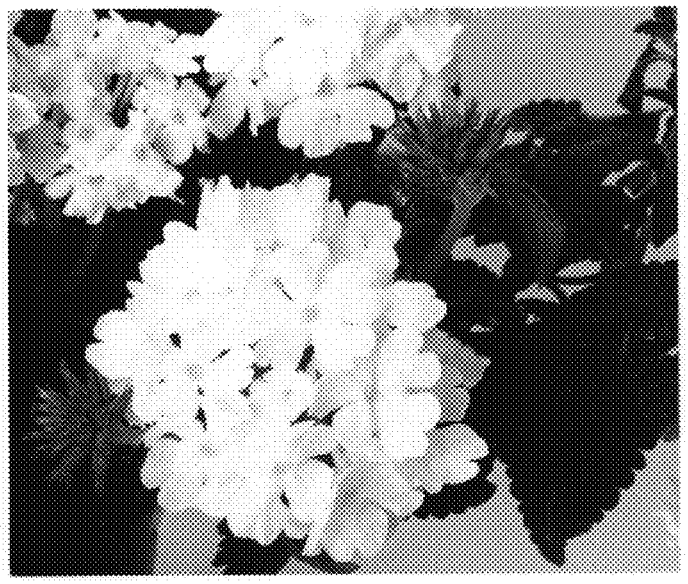
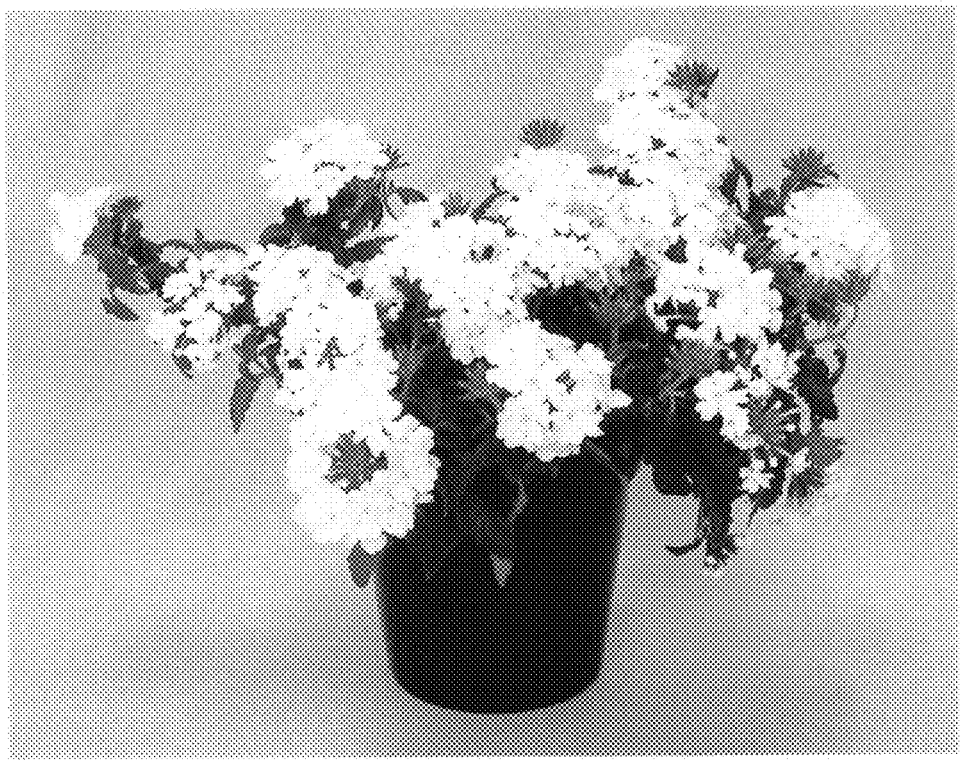

* * * * *